(12) United States Patent
Boix Bernardini

(10) Patent No.: US 8,598,363 B2
(45) Date of Patent: Dec. 3, 2013

US008598363B2

(54) PROCESS FOR MANUFACTURING 2-[(3,5-DIFLUORO-3'-METHOXY-1,1'BIPHENYL-4-YL)AMINO]NICOTINIC ACID

(75) Inventor: Maria Carmen Boix Bernardini, Barcelona (ES)

(73) Assignee: Almirall, S.A., Barcelona (ES)

(*) Notice: Subject to any disclaimer, the term of this patent is extended or adjusted under 35 U.S.C. 154(b) by 0 days.

(21) Appl. No.: 13/501,847

(22) PCT Filed: Oct. 14, 2010

(86) PCT No.: PCT/EP2010/006283
§ 371 (c)(1),
(2), (4) Date: Jun. 12, 2012

(87) PCT Pub. No.: WO2011/045059
PCT Pub. Date: Apr. 21, 2011

(65) Prior Publication Data
US 2012/0245359 A1 Sep. 27, 2012

(30) Foreign Application Priority Data
Oct. 16, 2009 (EP) .................................. 09382212

(51) Int. Cl.
*C07D 213/80* (2006.01)
(52) U.S. Cl.
USPC ........................................................ 546/310
(58) Field of Classification Search
None
See application file for complete search history.

(56) References Cited

U.S. PATENT DOCUMENTS

| | | | |
|---|---|---|---|
| 5,780,592 | A | 7/1998 | Mullner et al. |
| 7,071,222 | B2 | 7/2006 | Bartlett et al. |
| 7,258,118 | B2 | 8/2007 | Goede et al. |
| 8,258,308 | B2 | 9/2012 | Castro Palomino Laria et al. |
| 2003/0004171 | A1 | 1/2003 | Humphrey et al. |
| 2006/0081246 | A1 | 4/2006 | Goede et al. |
| 2010/0074898 | A1 | 3/2010 | Castro Palomino Laria et al. |
| 2011/0129445 | A1 | 6/2011 | Godessart Marina et al. |
| 2011/0212945 | A1 | 9/2011 | Castro Palomino Laria et al. |
| 2011/0280831 | A1 | 11/2011 | Godessart Marina et al. |
| 2012/0003183 | A1 | 1/2012 | Garcia Gonzales et al. |
| 2012/0003184 | A1 | 1/2012 | Garcia Gonzales et al. |
| 2012/0014918 | A1 | 1/2012 | Perez Garcia et al. |

FOREIGN PATENT DOCUMENTS

| | | |
|---|---|---|
| EP | 0 780 128 | 6/1997 |
| WO | WO 97/34600 | 1/1997 |
| WO | WO 97/00703 | 9/1997 |
| WO | WO 99/45926 | 9/1999 |
| WO | WO 00/76489 | 12/2000 |
| WO | WO 02/080897 | 10/2002 |
| WO | WO 03/000325 | 1/2003 |
| WO | WO 03/006425 | 1/2003 |
| WO | WO 03/061742 | 7/2003 |
| WO | WO 2004/048314 | 6/2004 |
| WO | WO 2004/056746 | 7/2004 |
| WO | WO 2004/056747 | 7/2004 |
| WO | WO 2005/075410 | 8/2005 |
| WO | WO 2006/001961 | 1/2006 |
| WO | WO 2006/022442 | 3/2006 |
| WO | WO 2006/044741 | 4/2006 |
| WO | WO 2006/122788 | 11/2006 |
| WO | WO 2008/077639 | 7/2008 |
| WO | WO 2008/097180 | 8/2008 |
| WO | WO 2009/021696 | 2/2009 |
| WO | WO 2009/153043 | 12/2009 |
| WO | WO 2010/083975 | 7/2010 |
| WO | WO 2010/102824 | 9/2010 |
| WO | WO 2010/102825 | 9/2010 |
| WO | WO 2010/102826 | 9/2010 |

OTHER PUBLICATIONS

U.S. Appl. No. 12/520,237, filed Sep. 9, 2009, Castro Palomino Laria et al.
U.S. Appl. No. 12/672,725, filed Mar. 16, 2010, Castro Palomino Laria et al.
U.S. Appl. No. 12/999,698, filed Dec. 17, 2010, Godessart Marina et al.
U.S. Appl. No. 13/145,628, filed Jul. 21, 2011, Godessart Marina et al.
U.S. Appl. No. 13/256,104, filed Sep. 19, 2011, Garcia Gonzales et al.
U.S. Appl. No. 13/256,127, filed Sep. 19, 2011, Garcia Gonzales et al.
U.S. Appl. No. 13/256,349, filed Sep. 28, 2011, Perez Garcia et al.
Batt, DG "Inhibitors of dihydroorotate dehydrogenase," *Expert Opinion on Therapeutic Patents*, 9(1): 41-54 (1999).
Baughman, RP et al. "Leflunomide for Chronic Sarcoidosis," *Clinical Research*, 21: 43-48 (2004).
Berge, S.M. et al., "Pharmaceutical Salts", *Journal of Pharmaceutical Science*, American Pharmaceutial Association, Washington, DC, vol. 66, No. 1, Jan. 1, 1977, pp. 1-19, XP00562636, ISSN: 0022-3549.
Breedveld, FC et al. "Leflunomide: Mode of Action in the Treatment of Rheumatoid Arthritis," *Annals of the Rheumatic Diseases*, 59: 841-849 (2000).
ClinialTrials.gov Identifier: NCT00637819, Sanofi-Aventis, Double blind, randomized, placebo controlled pilot study of leflunomide in systemic lupus erythematosus (SLE) (2008).
Cutolo, M. et al. "Anti-inflammatory mechanisms of methotrexate in rheumatoid arthritis," *Ann. Rheum. Dis.*, 60:729-735 (2001).
Dexter, DL et al. "Activity of a Novel 4-Quinolinecarboxylic Acid, NSC 368390 [6-Fluoro-2-(2'-fluoro-1,1'-biphenyl-4-yl)-3-methyl-4-quinolinecarboxylic Acid Sodium Salt], against Experimental Tumors," *Cancer Research*, 45: 5563-5568 (Nov. 1985).
Dimitrova, P. et al. "Restriction of De Novo Primidine Biosynthesis Inhibits Th1 Cell Activation and Promotes Th2 Cell Differentiation," *The Journal of Immunology*, 169:3392-3399 (2002).
English-language Derwent Abstract for WO 06/022442, 2006.
English Language Caplus Abstract for Spano, R. et al. "Preparation and pharmacology of some derivatives of 2-aminonicotinic," *Farmaco, Edizione Scientifica*, Societa Chimica Italiana, Pavia, IT, 26(9): 844-849 (1971).
Fox, RI "Mechanism of Action of Leflunomide in Rheumatoid Arthritis," *The Journal of Rheumatology*, 25, Supplement 53:20-26 (1998).

(Continued)

*Primary Examiner* — Zinna Northington Davis
(74) *Attorney, Agent, or Firm* — Finnegan, Henderson, Farabow, Garrett & Dunner, LLP

(57) ABSTRACT

The present disclosure relates to a process for manufacturing 2-[(3,5-difluoro-3'-methoxy-1,1'biphenyl-4-yl)amino]nicotinic acid.

17 Claims, No Drawings

(56) References Cited

OTHER PUBLICATIONS

Gu, L. et al., "Preformulation Salt Selection. Physical Property Comparisons of the Tris (Hydroxymethyl) Aminomethane (THAM) Salts of Four Analgesic/Anti-inflammatory Agents with the Sodium Salts and the Free Acids," Pharmaceutical Research, Kluwer Academic Publishers, New York, NY, vol. 4, No. 3, Jan. 1, 1987, pp. 255-257, XP002099348, ISSN: 0724-8741.
Haibel, J. et al. "Six Month Open Label Trial of Leflunomide in Active Ankylosing Spondylitis," *Annals of the Rheumatic Diseases*, 64: 124-126 (2005).
International Search Report mailed May 8, 2008, for International Application No. PCT/EP2007/011401 (WO 2008/077639 A1).
International Search Report mailed Oct. 20, 2008, for International Application No. PCT/EP2008/006573 (WO 2009/021696).
International Search Report mailed Jul. 31, 2009, for International Application No. PCT/EP2009/004404 (WO 2009/153043).
International Search Report mailed Apr. 16, 2010, for International Application No. PCT/EP2010/000270 (WO 2010/083975).
International Search Report mailed May 31, 2010, for International Application No. PCT/EP2010/001549 (WO 2010/102825).
International Search Report mailed Nov. 18, 2010, for International Application No. PCT/EP2010/001548 (WO 2010/102824).
International Search Report mailed Apr. 23, 2010, for International Application No. PCT/EP2010/001550 (WO 2010/102826).
John, GT et al. "Leflunomide Therapy for Cytomegalovirus Disease in Renal Allograft Recipients," *Transplantation*, 77(9): 1460-1461 (2003).
Kermack, WO "Some Anilinopyridine Derivatives," *Journal of the Chemical Society*, pp. 726-727 (1942).
Kremer, JM "Concomitant Leflunomide Therapy in Patients with Active Rheumatoid Arthritis despite Stable Doses of Methotrexate," *Annals of Internal Medicine*, 137(9): 726-733 (2002).
Kremer, JM "Methotrexate and leflunomide: Biochemical basis for combination therapy in the treatment of rheumatoid arthritis," *Seminars in Arthritis and Rheumatism*, 29(1): 14-26 (1999).
Kulkarni, OP et al. "4SC-101, A Novel Small Molecule Dihydroorotate Dehydrogenase Inhibitor, Suppresses Systemic Lupus Erythematosus in MRL-(Fas)lpr Mice," *The American Journal of Pathology*, 176(6): 2840-2847 (2010).
Leban, J. et al. "Biphenyl-4-ylcarbamoyl thiophene carboxylic acids as potent DHODH inhibitors," *Bioorganic & Medicinal Chemistry Letters*, 16(2): 267-270 (2006).
Liu, S. et al. "Structures of Human Dihydroorotate Dehydrogenase in Complex with Antiproliferative Agents," *Structure*, 8(1): 25-33 (2000).
Löffler, M. et al. "Dihydroorotat-ubiquinone oxidoreductase links mitochondria in the biosynthesis of pyrimidine nucleotides," *Molecular and Cellular Biochemistry*, 174: 125-129 (1997).
Majithia, V, et al. "Successful Treatment of Sarcoidosis with Leflunomide," *Rheumatology*, 42: 700-702 (2003).
Manna, SK et al. "Leflunomide Suppresses TNF-Induced Cellular Responses: Effects on NF-{kappa}B, Activator Protein-1, c-Jun N-Terminal Protein Kinase, and Apoptosis," *Journal of Immunology*, 165:5962-5969 (2000).
McRobert, L. et al. "RNA Interference (RNAi) Inhibits Growth of *Plasmodium falciparum*," *Molecular & Biochemical Parasitology*, 19: 273-278 (2002).
Mehta, V. et al. "Leflunomide," *Indian J. Dermatol. Venereol. Leprol.*, 75(4): 422-425 (2009).
Metzler, C. et al. "Maintenance of Remission with Leflunomide in Wegener's Granulomatosis," *Rheumatology*, 43:315-320 (2004).
Miyaura, N. et al. "Palladium-Catalyzed Cross-Coupling Reactions of Organoboron Compounds," *Chemical Reviews*, 35:2457-2483 (1995).
Notice of Allowance dated May 2, 2012, in U.S. Appl. No. 12/520,237.
Notice of Allowability (Corrected) dated Jun. 26, 2012, in U.S. Appl. No. 12/520,237.

O'Connor, PW et al. "A Phase II Study of the Safety and Efficacy of Teriflunomide in Multiple Sclerosis with Relapses," *Neurology*, 66:894-900 (2006).
Office Action (Restriction Requirement) dated Sep. 13, 2012, in U.S. Appl. No. 13/145,628.
Office Action dated Sep. 28, 2012, in U.S. Appl. No. 12/999,698.
Office Action dated Feb. 28, 2011, in U.S. Appl. No. 12/520,237.
Office Action (Restriction Requirement) dated Jun. 12, 2012, in U.S. Appl. No. 12/672,725.
Office Action dated Jun. 2, 2011, in U.S. Appl. No. 12/520,237.
Office Action dated Nov. 4, 2011, in U.S. Appl. No. 12/520,237.
Office Action (Restriction Requirement) dated Jun. 4, 2012, in U.S. Appl. No. 12/999,698.
Office Action dated Jul. 30, 2012, in U.S. Appl. No. 12/672,725.
Phillips, Margaret A. et al., "Triazolopyrimidine-Based Dihydroorotate Dehydrogenase Inhibitors with Potent and Selective Activity Against the Malaria Parasite *Plasmodium falciparum*", *J. Med. Chem.*, 51: 3649-3653 (2008).
Sanders, S. et al. "Leflunomide for the Treatment of Rheumatoid Arthritis and Autoimmunity," *American Journal of the Medical Sciences*, 323(4): 190-193 (2002).
Schläpfer, E. et al. "Anti-HIV-1 Activity of Leflunomide: a Comparison with Mycophenolic Acid and Hydroxyurea," *AIDS*, 17(11): 1613-1620 (2003).
Silverman, E. et al. "Long-Term Open-Label Preliminary Study of the Safety and Efficacy of Leflunomide in Patients with Polyarticular-Course Juvenile Rheumatoid Arthritis," *Arthritis & Rheumatism*, 52(2): 554-562 (2005).
Silverman, RB "The Organic Chemistry of Drug Design and Drug Action," Chapter 2, Section 2.2, pp. 29-32, Elsevier Academic Press (2004).
Spano, R. et al. "Preparation and pharmacology of some derivatives of 2-aminonicotinic," Farmaco, Edizione Scientifica, Societa Chimica Italiana, Pavia, IT, 26(9): 844-849 (1971).
Stahl, P.H. et al., "Tromethamine", *Handbook of Pharmaceutical Salts Properties, Selection and Use*, Jan. 1, 2002, pp. 324-325, XP002214621.
Tlacuilo Parra, JA et al. "Leflunomide in the treatment of psoriasis: results of a phase II open trial," *British Journal of Dermatology*, 150: 970-976 (2004).
Urushibara, M. et al. "The Antirheumatic Drug Leflunomide Inhibits Osteoclastogenesis by Interfering With Receptor Activator of NF-κB Ligand-Stimulated Induction of Nuclear Factor of Activated T Cells c1," *Arthritis & Rheumatism*, 50(3): 794-804 (2004).
Vyas, V.K. et al., "Recent Developments in the Medicinal Chemistry and Therapeutic Potential of Dihydroorotate Dehydrogenase (DHODH) Inhibitors", *Mini-Reviews in Medicinal Chemistry*, 11: 1039-1055 (2011).
Wahl, C. et al. "Sulfasalazine: a Potent and Specific Inhibitor of Nuclear Factor Kappa B," *J. Clin. Invest.*, 101(5): 1163-1174 (1998).
Weinblatt, ME et al. "Pharmacokinetics, safety, and efficacy of combination treatment with methotrexate and leflunomide in patients with active rheumatoid arthritis," *Arthritis & Rheumatism*, 42(7): 1322-1328 (Jul. 1999).
Ando et al., in Remington: The Science and Practice of Pharmaoy. 20th Edition. Alfonso R, Gennaro (Ed.), Philadelphia, PA: Lippincott Williams & Wilkins, 2000: pp. 704-712.
Bastin, R.J. et al., "Salt Selection and Optimisation Procedures for Pharmaceutical New Chemical Entities" Organic Process Research & Development (2000) 4:427-435.
Grigor'eva et al., "Catalytic activity of complexes of copper(II) with carboxyphenylaminopyrimidines (Antiphlogistics) in model reactions of oxidase and catalase type", Khimiko-Farmatsevticheskii Zhurnal (1978), 12(4), pp. 7-14.
English translation of Grigor'eva, "Catalytic activity of complexes of copper(II) with carboxyphenylaminopyrimidines (Antiphlogistics) in model reactions of oxidase and catalase type," Khimiko-Farmatsevticheskii Zhurnal (1978) 12(4):pp. 7-14.
Morissette, S.L. et al. "High-throughput crystallization: polymorphs, salts, co-crystals and solvates of pharmaceutical solids," Advanced Drug Delivery Reviews, 56:275-300 (2004).

(56) References Cited

OTHER PUBLICATIONS

Mroczkowski, P.J. et al., "Methotrexate and leflunomide combination therapy for patients with active rheumatoid arthritis", Clin. Exp. Rheumatol, 1999, 17(Suppl. 18): S66-S68.
Notice of Allowance dated May 14, 2013, in U.S. Appl. No. 12/672,725.
Notice of Allowance dated May 1, 2013, in U.S. Appl. No. 13/256,127.
Office Action (Restriction Requirement) dated Jun. 14, 2012, in U.S. Appl. No. 13/256,127.
Office Action dated Sep. 21, 2012, in U.S. Appl. No. 13/256,127.
Office Action (Restriction Requirement) dated Apr. 2, 2013, in U.S. Appl. No. 13/567,437.
Office Action (Restriction Requirement) dated Apr. 12, 2013, in U.S. Appl. No. 13/256,349.
Office Action dated May 17, 2013, in U.S. Appl. No. 13/567,437.
Office Action (Restriction Requirement) dated May 17, 2013, in U.S. Appl. No. 12/999,698.
Patani et al., "Bioisosterism: A Rational Approach in Drug Design," Chem. Rev. 1996, 3147-3176.
Saag, K. et al. "American College of Rheumatology 2008 Recommendations for the Use of Nonbiologic and Biologic Disease-Modifying Antirheumatic Drugs in Rheumatoid Arthritis" Arthritis & Rheumatism 59 (6), 762-784 (2008).
Silverman, R. B. "The Organic Chemistry of Drug Design and Drug Action," Chapter 2, Section 2.1, pp. 9, Elsevier Academic Press (2004).
Swierkot, Jerzy et al., Methotrexate in rheumatoid arthritis, Pharmacological Reports, Institute of Pharmacological Polish Academy of Sciences, 2006, 58.473-492.
Vippagunta, S.R. et al. "Crystalline Solids," Advanced Drug Delivery Reviews, 48:3-26 (2001).
International Search Report for International Application No. PCT/EP2010/006283, mailed Nov. 12, 2010.

PROCESS FOR MANUFACTURING 2-[(3,5-DIFLUORO-3'-METHOXY-1,1'BIPHENYL-4-YL)AMINO]NICOTINIC ACID

This application is a national stage filing under 35 U.S.C. §371 of International Application No. PCT/EP2010/006283 filed on 14 Oct. 2010, which claims priority of European Patent Application No. 09382212.0, filed on 16 Oct. 2009. The contents of both applications are incorporated herein by reference.

The present invention relates to a process for the manufacture of 2-[(3,5-difluoro-3'-methoxy-1,1'-biphenyl-4-yl)amino]nicotinic acid.

This compound, which has the structure of formula (I), as well as a process for its manufacture, is described in the international patent application WO 2008/077639 A1.

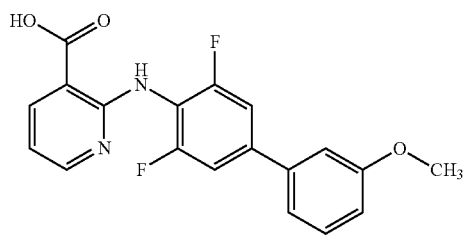

(I)

It is generally known that impurities present in pharmaceutical substances should, due to the regulatory restrictions associated to the pharmaceutical substances, be reduced or, if possible, eliminated.

In particular, the Guideline on the Specification Limits for Residues of Metal Catalysts or Metal Reagents from the European Medicines Agency (EMEA), establishes a concentration limit for metal residues present in pharmaceutical substances due to the use of a specific metal catalyst or metal reagent in synthetic processes for the manufacture said pharmaceutical substances.

Additionally, the Guideline on the Limits of Genotoxic Impurities of the Committee for Medicinal Products for Human Use (CHMP) from the European Medicines Agency (EMEA) sets concentration limits of genotoxic impurities in drug substances. Some of the impurities which often reside in pharmaceutical substances are potentially genotoxic (reagents, intermediates or by-products) either because they are known as genotoxic and/or carcinogenic (e.g. alkylating agents) or because they are substances which show "alerting structure" in terms of genotoxicity (Judson P, *J Toxicol Sci*, 2002, 27(4), 278) WO 2008/077639 A1 describes a two steps process for the manufacture of 2-[(3,5-difluoro-3'-methoxy-1,1'-biphenyl-4-yl)amino]nicotinic acid:

Step a)

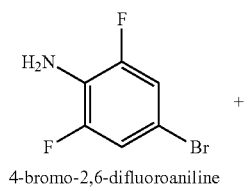

4-bromo-2,6-difluoroaniline

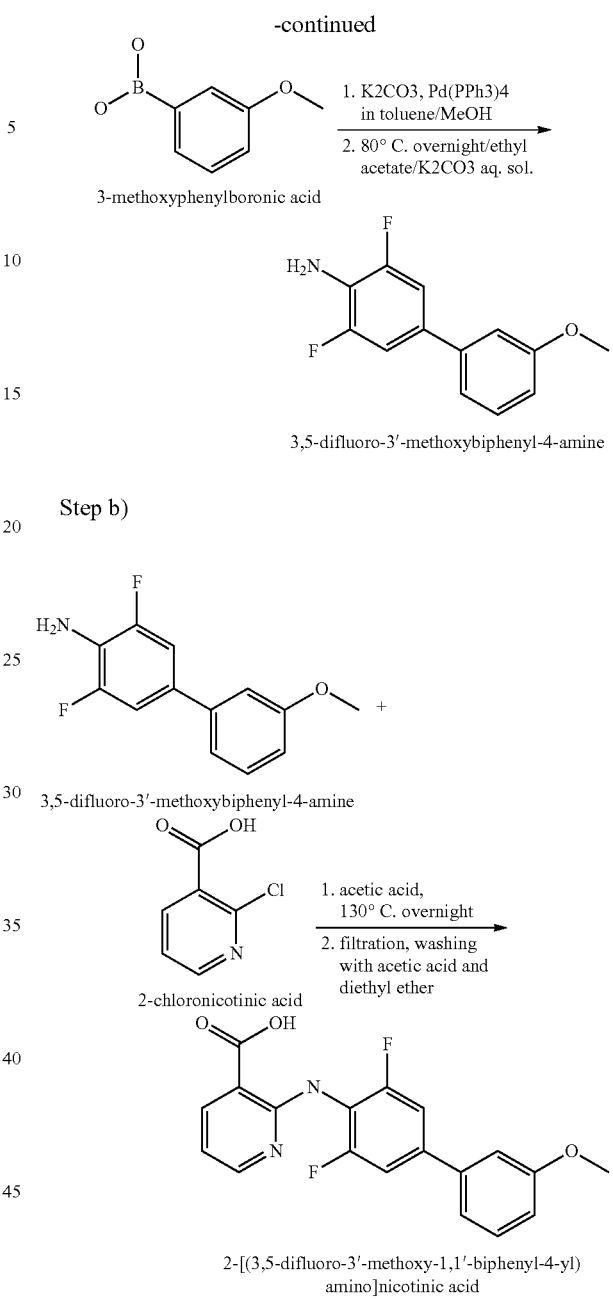

The inventors have now unexpectedly found that, by proper selection of the reaction conditions, particularly by forming and isolating an aminium salt of 3,5-difluoro-3'-methoxybiphenyl-4-amine, the process described in WO 2008/077639 A1 can be optimized to decrease the content of impurities, which can be metal residues from metal-based catalysts, by-products of the reaction process or non-reacted intermediates suspected to be genotoxic, while maintaining or increasing the reaction yield.

The inventors have also unexpectedly found that by using a Pd/C catalyst for the coupling reaction between 4-bromo-2,6-difluoroaniline and 3-methoxyphenylboronic acid, the yield of the overall reaction can be increased significantly compared with the process described in WO 2008/077639.

A first aspect of the invention therefore provides a process for manufacturing 2-[(3,5-difluoro-3'-methoxy-1,1'-biphenyl-4-yl)amino]nicotinic acid, which comprises the steps of:

a) providing 3,5-difluoro-3'-methoxybiphenyl-4-amine,
b) preparing and isolating an aminium salt of the 3,5-difluoro-3'-methoxybiphenyl-4-amine, and
c) further reacting the aminium salt of 3,5-difluoro-3'-methoxybiphenyl-4-amine obtained in b) to obtain 2-[(3,5-difluoro-3'-methoxy-1,1'-biphenyl-4-yl)amino] nicotinic acid.

A further aspect of the invention provides a process for manufacturing 2-[(3,5-difluoro-3'-methoxy-1,1'-biphenyl-4-yl)amino]nicotinic acid, which comprises the steps of:
i) reacting 4-bromo-2,6-difluoroaniline with 3-methoxyphenylboronic acid in the presence of a Pd/C catalyst to obtain 3,5-difluoro-3'-methoxybiphenyl-4-amine, and
ii) further reacting the 3,5-difluoro-3'-methoxybiphenyl-4-amine obtained in step i) to obtain 2-[(3,5-difluoro-3'-methoxy-1,1'-biphenyl-4-yl)amino]nicotinic acid.

A further aspect of the invention provides a compound of formula (I):

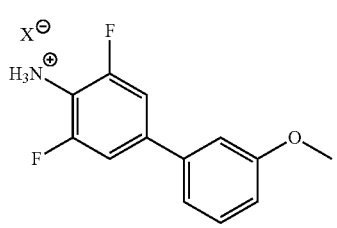

(I)

wherein $X^-$ is the anion of a mineral acid or an organic acid.

Typically, in step a), 3,5-difluoro-3'-methoxybiphenyl-4-amine is obtained by reacting 4-bromo-2,6-difluoroaniline with 3-methoxyphenylboronic acid. Step a) of the process typically corresponds to a coupling reaction of an haloarene with an arylboronic acid and can be carried out under the conditions of the Suzuki reaction (Miyaura, N.; Suzuki, A. Chem. Rev. 1995, 95, 2475) or as described in WO 2008/077639 A1. Typically said reaction is catalyzed by palladium catalysts such as [1,1'-bis(diphenylphosphino)-ferrocene] dichloropalladium (II) complex with dichloromethane (1:1), tetrakis(triphenylphosphine)-palladium(0), bis(triphenylphosphine)palladium(II) chloride or tris(dibenzylidene-acetone)-dipalladium(0) in a aprotic organic solvent such as dioxane, toluene, dimethylformamide (DMF) or dimethoxyethane (DME) and in the presence of a base such as cesium carbonate, sodium carbonate, potassium carbonate or potassium phosphate at a temperature from 70 to 140° C.

In a preferred embodiment, step a), i.e. reacting 4-bromo-2,6-difluoroaniline with 3-methoxyphenylboronic acid to obtain 3,5-difluoro-3'-methoxybiphenyl-4-amine is catalyzed by a heterogeneous palladium supported on carbon catalyst (Pd/C catalyst). Typically in said Pd/C catalyst the molar ratio palladium to carbon ranges from 0.5 to 20%, preferably from 1 to 15%. Typically, Pd/C catalyst is applied suspended in aqueous sodium carbonate or potassium carbonate solution. The Pd/C catalyst is typically loaded in an amount which ranges from 1 to 20 wt. % of the substrate, preferably from 2 to 15 wt. %. If step a) is catalyzed by a Pd/C catalyst a polar solvent such as water, methanol, ethanol, n-propanol, isopropanol, n-butanol, isobutanol, sec-butanol, tert-butanol, n-pentanol, tert-pentyl alcohol (tert-amyl alcohol), ethylene glycol, propylene glycol, dipropylene glycol or glycerol can be present in the reaction medium. A particularly preferred solvent is ethanol.

Typically, 3,5-difluoro-3'-methoxybiphenyl-4-amine obtained in step a) is isolated and purified using standard purification techniques before conducting step b), i.e. the formation of the aminium salt (i.e. non-quaternary ammonium salt). Standard purification techniques are described in *Purification of Laboratory Chemicals*, third edition, 1988, Ed. Pergamon Press, and include acid-base extraction in a solvent and subsequent distillation of said solvent.

The aminium salt from step b) is typically formed by mixing a mineral acid or an organic acid with 3,5-difluoro-3'-methoxybiphenyl-4-amine, preferably by mixing said acid with a solution or suspension of 3,5-difluoro-3'-methoxybiphenyl-4-amine in a solvent or mixture of solvents selected from the group consisting of $C_5$-$C_8$ alkanes, $C_1$-$C_8$ haloalkanes, alcohols, esters, ethers, water and mixtures thereof.

According to the invention the term mineral acid refers to an acid derived by chemical reaction from inorganic minerals. Preferred mineral acids are selected from the group consisting of hydrobromic acid, hydrochloric acid, hydrofluoric acid, nitric acid, phosphoric acid, sulfuric acid and mixtures thereof.

According to the invention the term organic acid refers to an organic compound with acidic properties. Preferred organic acids are selected from the group consisting of cyclamic acid, ethane-1,2-disulfonic acid, methanesulfonic acid, naphthalene-1,5-disulfonic acid, naphthalene-2-sulfonic acid, thiocyanic acid, formic acid, acetic acid, p-toluenesulfonic acid, 4-chloro benzenesulfonic acid, 4-bromo benzenesulfonic acid and mixtures thereof.

Preferably, the acid is selected from the group consisting of hydrochloric acid, nitric acid, phosphoric acid, sulfuric acid, p-toluenesulfonic acid and mixtures thereof. Particularly preferred acids are hydrochloric acid, p-toluenesulfonic acid and mixtures thereof.

In a preferred embodiment, the acid (mineral or organic) is in the form of an aqueous solution. Typically, the concentration of said aqueous solution ranges from 5 to 50 wt. %, preferably from 10 to 40 wt. %.

Preferred solvents are selected from the group consisting of pentane, n-hexane, n-heptane, n-octane, chloromethane, dichloromethane, tetrachloromethane, ethanol, n-propanol, isopropanol, n-butanol, isobutanol, sec-butanol, t-butanol, n-pentanol, tert-pentyl alcohol (tert-amyl alcohol), ethylene glycol, propylene glycol, dipropylene glycol, glycerol, diethylene glycol monoethyl ether, n-propyl acetate, isopropyl acetate, butyl glycol acetate, water and mixtures thereof. Preferably, the solvent is selected from the group consisting of n-hexane, dichloromethane, ethylene glycol, propylene glycol, n-propyl acetate, isopropyl acetate, water and mixtures thereof. A particularly preferred solvent is isopropyl acetate.

In one embodiment the aminium salt from step b) is formed by mixing an acid selected from the group consisting of hydrochloric acid, nitric acid, phosphoric acid, sulfuric acid, p-toluenesulfonic acid and mixtures thereof in the form of a 5 to 50 wt. %, preferably a 10 to 40 wt. % aqueous solution with 3,5-difluoro-3'-methoxybiphenyl-4-amine.

In another embodiment the aminium salt from step b) is formed by mixing an acid selected from the group consisting of hydrochloric acid, nitric acid, phosphoric acid, sulfuric acid, p-toluenesulfonic acid and mixtures thereof in the form of a 5 to 50 wt. %, preferably a 10 to 40 wt. % aqueous solution with a solution or suspension of 3,5-difluoro-3'-methoxybiphenyl-4-amine in a solvent selected from the group consisting of n-hexane, dichloromethane, ethylene glycol, propylene glycol, n-propyl acetate, isopropyl acetate and mixtures thereof.

In a preferred embodiment, the ratio of volume of the solvent from step b) (in L) to the mass of 4-bromo-2,6-difluoroaniline from step a) (in Kg) ranges from 2:1 to 50:1, preferably from 4:1 to 25:1, more preferably from 5:1 to 18:1, even more preferably from 6:1 to 9:1. This ratio represents an optimum between yield and impurities. A higher solvent content would reduce the crystallization yield while a lower solvent content would increase the amount of impurities, in particular the content of palladium.

Typically, the aminium salt of 3,5-difluoro-3'-methoxybiphenyl-4-amine from step b) is isolated by filtration and washed with an appropriate solvent before conducting step c). Preferably said solvent corresponds to the solvent used in step b).

Typically, step c) comprises either c1) reacting the aminium salt of 3,5-difluoro-3'-methoxybiphenyl-4-amine obtained in step b) with 2-chloronicotinic acid, or c2) hydrolysing the aminium salt of 3,5-difluoro-3'-methoxybiphenyl-4-amine obtained in step b) to obtain 3,5-difluoro-3'-methoxybiphenyl-4-amine and reacting the thus-obtained 3,5-difluoro-3'-methoxybiphenyl-4-amine with 2-chloronicotinic acid.

In one embodiment (step c1), the aminium salt of 3,5-difluoro-3'-methoxybiphenyl-4-amine from step b) is dried or semidried to remove or partially remove the solvent and then it is reacted with 2-chloronicotinic acid to obtain 2-[(3,5-difluoro-3'-methoxy-1,1'-biphenyl-4-yl)amino]nicotinic acid.

In another embodiment (step c2), the aminium salt of 3,5-difluoro-3'-methoxybiphenyl-4-amine from step b) is optionally, dried or semidried to remove or partially remove the solvent. Subsequently, said aminium salt is hydrolyzed in the presence of water under well-known reaction conditions to 3,5-difluoro-3'-methoxybiphenyl-4-amine and finally, 3,5-difluoro-3'-methoxybiphenyl-4-amine in the amine form is reacted with 2-chloronicotinic acid to obtain 2-[(3,5-difluoro-3'-methoxy-1,1'-biphenyl-4-yl)amino]nicotinic acid.

According to the invention, it is preferred that step c1) or c2) takes place in a solvent or mixture of solvents. Typically, solvents are selected from the group consisting of ethanol, n-propanol, isopropanol, n-butanol, isobutanol, sec-butanol, t-butanol, n-pentanol, tert-pentyl alcohol (tert-amyl alcohol), ethylene glycol, propylene glycol, dipropylene glycerol, diethylene glycol monoethyl ether, tetrahydrofurane, 1,4-dioxane, 1,2-dioxane, 1,3-dioxane and mixtures thereof. Preferably solvents are selected from the group consisting of ethanol, ethylene glycol, propylene glycol, dipropylene glycol and mixtures thereof. A particularly preferred solvent is ethanol.

In one embodiment, step c2) can be carried out in water, preferably without isolating the 3,5-difluoro-3'-methoxybiphenyl-4-amine in the amine form obtained by hydrolysis reaction of the aminium salt.

According to the invention, it is preferred that in step c1) or c2) a mineral acid or an organic acid is added to the reaction mixture.

However, when step c2) takes place in water, a mineral acid or an organic acid can optionally be added to the reaction mixture.

Preferred mineral acids to be used in steps c1) or c2) are selected from the group consisting of hydrobromic acid, hydrochloric acid, hydrofluoric acid, nitric acid, phosphoric acid, sulfuric acid and mixtures thereof.

Preferred organic acids are selected from the group consisting of cyclamic acid, ethane-1,2-disulfonic acid, methanesulfonic acid, naphthalene-1,5-disulfonic acid, naphthalene-2-sulfonic acid, thiocyanic acid, formic acid, acetic acid, p-toluenesulfonic acid, 4-chloro benzenesulfonic acid, 4-bromo benzenesulfonic acid and mixtures thereof.

Preferably, the acid is selected from the group consisting of hydrochloric acid, nitric acid, phosphoric acid, sulfuric acid, p-toluenesulfonic acid and mixtures thereof. Particularly preferred acids are hydrochloric acid, p-toluenesulfonic acid and mixtures thereof.

In a preferred embodiment, the acid (mineral or organic) is in the form of an aqueous solution. Typically, the concentration of said aqueous solution ranges from 5 to 50 wt. %, preferably from 7 to 40 wt. °A, more preferably from 8 to 20 wt. %.

In a preferred embodiment, the volume ratio of the solvent to the acid ranges from 1:5 to 1:15, preferably from 1:2 to 1:10, more preferably from 1:1 to 1:5.

Typically, 2-[(3,5-difluoro-3'-methoxy-1,1'-biphenyl-4-yl)amino]nicotinic acid obtained in step c1) or c2) is further purified using standard purification techniques such as distillation of the solvent, filtration, extraction and/or lixiviation.

In one embodiment, the process of the invention comprises the steps of
a) reacting 4-bromo-2,6-difluoroaniline with 3-methoxyphenylboronic acid to obtain 3,5-difluoro-3'-methoxybiphenyl-4-amine,
b) forming and isolating an aminium salt of 3,5-difluoro-3'-methoxybiphenyl-4-amine obtained in step a), and
c1) reacting the aminium salt of 3,5-difluoro-3'-methoxybiphenyl-4-amine from step b) with 2-chloronicotinic acid, or
c2) hydrolysing the aminium salt of 3,5-difluoro-3'-methoxybiphenyl-4-amine from step b) to obtain 3,5-difluoro-3'-methoxybiphenyl-4-amine and reacting the thus-obtained 3,5-difluoro-3'-methoxybiphenyl-4-amine with 2-chloronicotinic acid.

In a preferred embodiment, the process for the manufacture of 2-[(3,5-difluoro-3'-methoxy-1,1'-biphenyl-4-yl)amino]nicotinic acid comprises the steps of:
a) reacting 4-bromo-2,6-difluoroaniline with 3-methoxyphenylboronic acid to obtain 3,5-difluoro-3'-methoxybiphenyl-4-amine,
b) forming and isolating an aminium salt of 3,5-difluoro-3'-methoxybiphenyl-4-amine obtained in step a) by mixing an acid selected from the group consisting of hydrochloric acid, nitric acid, phosphoric acid, sulfuric acid, p-toluenesulfonic acid and mixtures thereof with a solution or suspension of 3,5-difluoro-3'-methoxybiphenyl-4-amine in a solvent selected from the group consisting of n-hexane, dichloromethane, ethylene glycol, propylene glycol, n-propyl acetate, isopropyl acetate and mixtures thereof,
c1) reacting the aminium salt of 3,5-difluoro-3'-methoxybiphenyl-4-amine from step b) with 2-chloronicotinic acid.

According to the invention, it is preferred that in step c1) a mineral acid or an organic acid is added to the reaction mixture.

Preferred mineral acids are selected from the group consisting of hydrobromic acid, hydrochloric acid, hydrofluoric acid, nitric acid, phosphoric acid, sulfuric acid and mixtures thereof.

Preferred organic acids are selected from the group consisting of cyclamic acid, ethane-1,2-disulfonic acid, methanesulfonic acid, naphthalene-1,5-disulfonic acid, naphthalene-2-sulfonic acid, thiocyanic acid, formic acid, acetic acid, p-toluenesulfonic acid, 4-chloro benzenesulfonic acid, 4-bromo benzenesulfonic acid and mixtures thereof.

Preferably, the acid is selected from the group consisting of hydrochloric acid, nitric acid, phosphoric acid, sulfuric acid, p-toluenesulfonic acid and mixtures thereof. Particularly preferred acids are hydrochloric acid, p-toluenesulfonic acid and mixtures thereof.

In a preferred embodiment, the acid (mineral or organic) is in the form of an aqueous solution. Typically, the concentration of said aqueous solution ranges from 5 to 50 wt. %, preferably from 7 to 40 wt. %, more preferably from 8 to 20 wt. %.

According to the invention, it is preferred that step c1) takes place in a solvent or mixture of solvents.

Preferred solvents are selected from the group consisting of pentane, n-hexane, n-heptane, n-octane, chloromethane, dichloromethane, tetrachloromethane, ethanol, n-propanol, isopropanol, n-butanol, isobutanol, sec-butanol, t-butanol, n-pentanol, tert-pentyl alcohol (tert-amyl alcohol), ethylene glycol, propylene glycol, dipropylene glycol, glycerol, diethylene glycol monoethyl ether, n-propyl acetate, isopropyl acetate, butyl glycol acetate and mixtures thereof. Preferably, the solvent is selected from the group consisting of n-hexane, dichloromethane, ethylene glycol, propylene glycol, n-propyl acetate, isopropyl acetate, water and mixtures thereof. A particularly preferred solvent is isopropyl acetate.

In another preferred embodiment, the process for the manufacture of 2-[(3,5-difluoro-3'-methoxy-1,1'-biphenyl-4-yl)amino]nicotinic acid comprises the steps of:
a1) reacting 4-bromo-2,6-difluoroaniline with 3-methoxyphenylboronic acid to obtain 3,5-difluoro-3'-methoxybiphenyl-4-amine,
a2) purifying 3,5-difluoro-3'-methoxybiphenyl-4-amine,
b) forming and isolating an aminium salt of 3,5-difluoro-3'-methoxybiphenyl-4-amine obtained in step a2) by mixing an acid selected from the group consisting of hydrochloric acid, nitric acid, phosphoric acid, sulfuric acid, p-toluenesulfonic acid and mixtures thereof with a solution or suspension of 3,5-difluoro-3'-methoxybiphenyl-4-amine in a solvent selected from the group consisting of n-hexane, dichloromethane, ethylene glycol, propylene glycol, n-propyl acetate, isopropyl acetate and mixtures thereof,
c1) reacting the aminium salt of 3,5-difluoro-3'-methoxybiphenyl-4-amine from step b) with 2-chloronicotinic acid to obtain 2-[(3,5-difluoro-3'-methoxy-1,1'-biphenyl-4-yl)amino]nicotinic acid in a solvent or mixture of solvents and adding a mineral acid or organic acid to the reaction mixture,
d) purifying 2-[(3,5-difluoro-3'-methoxy-1,1'-biphenyl-4-yl)amino]nicotinic acid.

Typically, 3,5-difluoro-3'-methoxybiphenyl-4-amine (step a2) and 2-[(3,5-difluoro-3'-methoxy-1,1'-biphenyl-4-yl)amino]nicotinic acid (step d) are purified using standard purification techniques such as acid-base extraction in a suitable solvent. Additionally, subsequent distillation of said solvent may be carried out if needed.

The term distillation refers to method of separating mixtures based on differences in their volatilities in a boiling liquid mixture. Typically, distillation is used to eliminate the solvent.

The term acid-base extraction refers to a procedure using sequential liquid-liquid extractions to purify acids and bases from mixtures based on their chemical properties. Usually, the mixture is dissolved in a suitable solvent and poured into a separating funnel. An aqueous solution of the acid or base is added, and the pH of the aqueous phase is adjusted to bring the compound of interest into its required form. After shaking and allowing for phase separation, the phase containing the compound of interest is collected. The procedure is then repeated with this phase at the opposite pH range. The order of the steps is not important and the process can be repeated to increase the separation.

Typically, sodium carbonate, potassium carbonate, sodium hydroxide, potassium hydroxide, ammonia, sodium bicarbonate, potassium bicarbonate or mixtures thereof are used to adjust the pH to alkaline conditions. According to the invention, preferred bases are sodium carbonate, sodium hydroxide, ammonia or mixtures thereof. It is preferred that the base (or mixture of bases) is used in the form of aqueous solutions. Typically, the concentration of said aqueous solution ranges from 2 to 50 wt. %, preferably from 3 to 40 wt. %, more preferably from 3 to 30 wt. %.

Typically, citric acid, phosphoric acid, hydrochloric acid, nitric acid, sulfuric acid or mixtures thereof are used to adjust the pH to acidic conditions. According to the invention, preferred acids are hydrochloric acid, phosphoric acid, sulfuric acid or mixtures thereof. It is preferred that the acid (or mixture of acids) is used in the form of aqueous solutions. Typically, the concentration of said aqueous solution ranges from 5 to 50 wt. %, preferably from 10 to 40 wt. %.

Typically, suitable solvents to be used in the acid-base extraction are solvents non-miscible in water such as pentane, n-hexane, ciclohexane, n-heptane, n-octane, chloromethane, dichloromethane, tetrachloromethane, ethyl acetate, n-propyl acetate, isopropyl acetate, butyl glycol acetate and aromatic solvents such as benzene, toluene, ethylbenzene, chlorobenzene, p-xylene, m-xylene, o-xylene, styrene, isopropylbenzene, n-propylbenzene, 2-chlorotoluene, 3-chlorotoluene, 4-chlorotoluene, tert-butylbenzene, s-butylbenzene, isobutylbenzene, 1,3-dichlorobenzene, 1,4-dichlorobenzene, n-butylbenzene, 1,2-dichlorobenzene, 1,3-diisopropylbenzene, 1,4-diisopropylbenzene, 2-nitrotoluene, 3-nitrotoluene, 4-nitrotoluene and mixtures thereof. Preferred solvents are selected from the group consisting of n-hexane, ciclohexane, dichloromethane, ethyl acetate, n-propyl acetate, isopropyl acetate, toluene, 2-nitrotoluene, 3-nitrotoluene, 4-nitrotoluene and mixtures thereof.

In a preferred embodiment, 3,5-difluoro-3'-methoxybiphenyl-4-amine (step a2) is purified by acid-base extraction using 2 to 50 wt. %, preferably from 3 to 40 wt. %, more preferably from 3 to 30 wt. % of aqueous solutions of bases selected from sodium carbonate, sodium hydroxide, ammonia and mixtures thereof in a solvent selected from n-hexane, ciclohexane, dichloromethane, ethyl acetate, n-propyl acetate, isopropyl acetate and mixtures thereof, followed by a distillation of the solvent.

In a preferred embodiment, 2-[(3,5-difluoro-3'-methoxy-1,1'-biphenyl-4-yl)amino]nicotinic acid (step d) is purified by an acid-base extraction using 2 to 50 wt. %, preferably from 3 to 40 wt. %, more preferably from 3 to 30 wt. % of aqueous solutions of bases selected from sodium carbonate, sodium hydroxide, ammonia and mixtures thereof in a solvent selected from n-hexane, ciclohexane, p-xylene, m-xylene, o-xylene, toluene, 2-nitrotoluene, 3-nitrotoluene, 4-nitrotoluene and mixtures thereof; followed by precipitation using 5 to 50 wt.%, preferably 10 to 40 wt.% of aqueous solutions of acids selected from hydrochloric acid, phosphoric acid, sulfuric acid and mixtures thereof.

In another preferred embodiment, 2-[(3,5-difluoro-3'-methoxy-1,1'-biphenyl-4-yl)amino]nicotinic acid is further purified by subsequent lixiviation (step e) in a solvent or mixture of solvents having a boiling point of between 30 and 210° C.

The term lixiviation refers to the process of separating soluble from insoluble substances by dissolving the former in water or some other solvent.

In a preferred embodiment, in the lixiviation step (e) the solvent or mixture of solvents having a boiling point of between 30 and 210° C. are selected from the group consisting of ketones, ethers including cyclic ethers, $C_5$-$C_8$ alkanes including $C_5$-$C_8$ cicloalkanes and alcohols.

The following are some examples of solvents that can be used for carrying out the lixiviation: acetone, methyl ethyl ketone (MEK), methyl isobutyl ketone (MIK), phenyl ethyl ketone, cyclopentanone, dioxane, tetrahydrofurane, ethyltetrahydrofurane, ethyltetrahydrofurane, n-pentane, n-hexane, n-heptane, n-octane, ciclopentane, ciclohexane, methanol, ethanol, n-propanol, isopropanol, n-butanol, sec-butanol, tert-butanol and tert-pentyl alcohol (tert-amyl alcohol). Preferred solvents are selected from the group consisting of acetone, n-hexane or ethanol. A particularly preferred solvent is acetone.

Step (i) of the process of the invention is catalyzed by a heterogeneous palladium supported on carbon catalyst (Pd/C catalyst). Typically in said Pd/C catalyst the molar ratio palladium to carbon ranges from 0.5 to 20%, preferably from 1 to 15%. Typically, Pd/C catalyst is applied suspended in aqueous sodium carbonate or potassium carbonate solution. The Pd/C catalyst is typically loaded in an amount which ranges from 1 to 20 wt. % of the substrate, preferably from 2 to 15 wt. %. A polar solvent such as water, methanol, ethanol, n-propanol, isopropanol, n-butanol, isobutanol, sec-butanol, tert-butanol, n-pentanol, tert-pentyl alcohol (tert-amyl alcohol), ethylene glycol, propylene glycol, dipropylene glycol or glycerol is typically present in the reaction medium. A particularly preferred solvent is ethanol.

Step (ii) of the process of the invention typically comprises steps b) and c) as defined above. Thus, step (ii) of the process of the invention typically compises the steps of:

b) forming and isolating an aminium salt of 3,5-difluoro-3'-methoxybiphenyl-4-amine provided in step a), and
c) further reacting the aminium salt of 3,5-difluoro-3'-methoxybiphenyl-4-amine obtained in b) to obtain 2-[(3,5-difluoro-3'-methoxy-1,1'-biphenyl-4-yl)amino]nicotinic acid.

Preferred embodiments of steps b) and c) are defined above.

In the compound of the present invention, $X^-$ is typically the anion of a mineral acid or organic acid described above. $X^-$ is preferably $Cl^-$.

The following examples show illustrative methods for preparing compounds according to the present invention, and are not intended to limit the scope of the invention.

EXAMPLES

Example 1

1) Preparation of 3,5-difluoro-3'-methoxybiphenyl-4-amine (Step a)

10 kg of 4-bromo-2,6-difluoroaniline (48.08 mol) and 67 L of toluene were charged into a reactor under nitrogen atmosphere and stirred at 20° C. until complete dissolution. 1.67 kg of Pd(PPh$_3$)$_4$ (1.44 mol) were charged and stirred for 10 min. 48 L of a 20 wt. % aqueous solution of Na$_2$CO$_3$ were then charged, followed by the addition of a solution of 3-methoxyboronic acid (8.77 kg, 57.7 mol) in methanol (32 L) over 20 minutes. The mixture was heated at 72° C. for 4 hours and then cooled to 20° C.

2) Purification of 3,5-difluoro-3'-methoxybiphenyl-4-amine 2.1. A solution of 123 L of a 10% aqueous solution of Na$_2$CO$_3$, 1.5 L of a 25 wt. % aqueous solution of ammonia and 2.0 kg of a filtration resin (Dicalite) were charged to the reactor and the mixture stirred for 5 minutes. The mixture was recirculated through a filter until clarification of the liquors (35 min) and charged into a reactor. 60 L of isopropyl acetate were added and the mixture was stirred for 10 minutes and the phases (A1+O1) were allowed to separate. The aqueous phase (A1) was transferred to a different reactor and 60 L of isopropyl acetate were charged. The mixture was stirred and the phases (A2+O2) were allowed to separate. Both organic phases (O1+O2) were charged into a reactor and 108 L of a 10 wt. % aqueous solution of Na$_2$CO$_3$ were added. The mixture was stirred and the phases (A3+O3) were allowed to separate. The organic phase (O3) was stirred with 108 L of a 10 wt. % aqueous solution of Na$_2$CO$_3$ and the phases (A4+O4) were allowed to separate. The organic phase (O4) was stirred with 100 L demineralised water and the phases (A5+O5) were allowed to separate. The organic phase (O5) was filtered over a filtration resin (Dicalite) in a filter and charged in to a reactor.

2.2. Distillation: The organic phase (O5) was distilled during 2 hours under reduced pressure (approx. 750 mm Hg) keeping the distilled mixture at temperature below 65° C.

3) Preparation of the Aminium Salt (Step b)

The distillation residue was dissolved in 100 L of isopropyl acetate, the mixture was cooled to 0-5° C. and 4.2 L of a 35 wt. % aqueous solution of HCl were added drop-wise until the pH was lower than 2. The aminium salt precipitated as a white solid from the dark brown coloured solution. The slurry was stirred for 2 hours at 0-5° C., filtered and the cake washed twice with 50 L of previously cooled isopropyl acetate. The cake was pulled dry under reduced pressure. 3,5-difluoro-3'-methoxybiphenyl-4-aminium chloride was isolated as beige solid. The weight of the wet-cake was 13.83 kg, equivalent to 10.25 kg of dry product (37.73 mol) which corresponds to a yield of 78.5%.

4) Preparation of 2-[(3,5-difluoro-3'-methoxy-1,1'-biphenyl-4-yl)amino]nicotinic acid (Step c1)

3,5-difluoro-3'-methoxybiphenyl-4-aminium chloride as wet cake (equivalent to 10.25 kg dry, 37.73 mol) and 30 L of ethanol 96% were charged into a reactor and stirred vigorously (150 rpm) at 20° C. Then, the following materials were charged: 100 L of a 10 wt. % aqueous solution of HCl, 3.5 kg of p-toluenesulfonic acid (18.4 mol) and 11.6 kg of 2-chloronicotinic acid (73.6 mol). The slurry was heated to reflux (90-95° C.) under vigorous stirring. After 8 hours of reaction, 2.9 kg of 2-chloronicotinic acid (18.4 mol) were charged and the mixture was stirred for a further 8 hours.

The reaction was distilled until a distillation temperature of 100° C. was reached, ensuring that all the ethanol had been removed. After complete distillation of ethanol, 150 L of demineralised water were added, the mixture was heated to 95° C. and the hot slurry was filtered at 95° C. in a closed filter. The cake was washed twice with hot water (2×100 L).

5) Purification of 2-[(3,5-difluoro-3'-methoxy-1,1'-biphenyl-4-yl)amino]nicotinic acid 5.1. A mixture of 80 L of a 4 wt. % aqueous solution of NaOH and 50 L of toluene previously cooled to 15° C. were recirculated through the filter until complete dissolution of the cake and charged into a reactor. The layers were allowed to separate (A1+O1). The aqueous phase (A1) was stirred with 50 L of toluene and the layers were allowed to separate (A2+O2), and the aqueous phase (A2) was filtered over a filtration resin (Dicalite) and charged into a reactor. The filter was washed with 10 L of a 4 wt. % aqueous solution of NaOH, and 15 L of demineralised water, and both filtrates were charged to the reactor which contained the aqueous phase A2.

The aqueous phase A2 was cooled to 0-5° C. and a HCl in the form of a 35 wt. % aqueous solution was added keeping the reaction temperature below 15° C. until the pH of the mixture was 1. The slurry was stirred for 1 hour, filtered and the cake washed three times with previously cooled demineralised water (3×100 L).

5.2. The solid was suspended in 80 L acetone, refluxed for 30 min and the mixture allowed to cool to 0-5° C. After 1 hour, the slurry was filtered and the cake washed twice with previously cooled acetone (2×10 L).

The cake was dried at 60° C. under reduced pressure until constant weight and was milled at 1600 rpm using a 0.8 mm sieve.

2-[(3,5-difluoro-3'-methoxy-1,1-biphenyl-4-yl)amino]nicotinic acid was isolated as a white solid yielding 8.9 kg (24.98 mol) which corresponds to a yield of 66.2%.

Example 2

1) Preparation of 3,5-difluoro-3'-methoxybiphenyl-4-amine (Step a) Using a Pd/C Catalyst 100 g of 4-bromo-2,6-difluoroaniline (0.481 mol) were dissolved in 750 mL of ethanol 96% under nitrogen atmosphere and stirred at 20° C. for 15 minutes. Then, 38.85 g (18 mmol, 3.75% molar) of Pd/C 50 wt. % wet were added followed by the addition of 1.25 L of a 20 wt. % aqueous solution of $Na_2CO_3$ keeping the reaction temperature below 30° C. Finally, 87.67 g (0.577 mmol, 1.2 eq) of 3-methoxyboronic acid were added and the reaction heated to 60° C. for 8 hours and then cooled to 20° C.

2) Purification of 3,5-difluoro-3'-methoxybiphenyl-4-amine 2.1. 600 mL of isopropyl acetate were added and the mixture was stirred for 10 minutes and the phases (A1+O1) were allowed to separate. The aqueous phase (A1) was stirred with 600 mL of isopropyl acetate for 10 minutes and the phases (A2+O2) were allowed to separate. Both organic phases (O1+O2) were stirred with 600 mL demineralised water and the phases (A3+O3) were allowed to separate. The organic phase (O3) was filtered over a filtration resin (Dicalite) in a filter.

2.2. Distillation: The organic phase (O3) was distilled under reduced pressure (approx. 750 mm Hg) keeping the distilled mixture at temperature below 65° C. to yield a dark coloured oil residue.

3) Preparation of the Aminium Salt (Step b)

The distillation residue was dissolved in 800 L of isopropyl acetate (8 vol/w), the mixture was cooled to 0-5° C. and 50 mL of a 35 wt. % aqueous solution of HCl were added dropwise until the pH was lower than 2. The aminium salt precipitated as a white solid from the dark brown coloured solution. The slurry was stirred for 2 hours at 0-5° C., filtered and the cake washed twice with 50 mL of previously cooled isopropyl acetate. The cake was pulled dry under reduced pressure and dried at 60° C. under reduced pressure (approx. 750 mm Hg) to constant weight. A total of 117 g (0.431 mmol, 89% yield) of 3,5-difluoro-3'-methoxybiphenyl-4-aminium chloride were isolated as beige solid.

4) Preparation of 2-[(3,5-difluoro-3'-methoxy-1,1'-biphenyl-4-yl)amino]nicotinic acid (Step c1)

The experimental procedure described in Example 1 was followed.

5) Purification of 2-[(3,5-difluoro-3'-methoxy-1,1'-biphenyl-4-yl)amino]nicotinic acid The cake was suspended in acetone. The solid was suspended in 650 mL acetone, refluxed for 30 min and the mixture allowed to cool to 0-5° C. After 1 hour, the slurry was filtered and the cake washed twice with previously cooled acetone (2×65 mL).

2-[(3,5-difluoro-3'-methoxy-1,1'-biphenyl-4-yl)amino]nicotinic acid was isolated as a white solid yielding 129 g (0.362 mol, 84% yield) which corresponds to an overall yield of 75%.

Comparative Example 1

33.44 g of 2-[(3,5-difluoro-3'-methoxy-1,1'-biphenyl-4-yl)amino]nicotinic acid, which corresponds to a yield of 53.4%, were obtained and purified following the process described in WO 2008/077639 A1.

The total impurities' content and the palladium content of 2-[(3,5-difluoro-3'-methoxy-1,1'-biphenyl-4-yl)amino]nicotinic acid obtained in Examples 1 and 2 (according to the invention) and Comparative Example 1 (C1) are indicated in Table 1. Said impurities were determined by High Performance Liquid Chromatograph (HPLC) and/or Capillary electrophoresis (CE). Additionally, the reaction yield is also indicated.

TABLE 1

Impurities' content and reaction yield of the different processes

| Example | Pd content (ppm) | Total impurities' content (excluding Pd)[1] (%) | Overall Reaction yield (%) |
|---|---|---|---|
| 1 | <2 | 0.10 | 66.2 |
| 2 | <10 | 0.20 | 75.0 |
| C1 | 100 | 0.46 | 53.4 |

[1]wt. % with respect to the total weight of 2-[(3,5-difluoro-3'-methoxy-1,1'-biphenyl-4-yl)amino]nicotinic acid From the experimental results it can be concluded that the process according to the invention allows a reduction in the content of impurities in 2-[(3,5-difluoro-3'-methoxy-1,1'-biphenyl-4-yl)amino]nicotinic acid, while increasing the reaction yield. This reduction of impurities is particularly evident in the case of the Pd content.

Additionally, when the coupling step between 4-bromo-2,6-difluoroaniline and 3-methoxyphenylboronic acid to obtain 3,5-difluoro-3'-methoxybiphenyl-4-amine is catalyzed by a Pd/C catalyst the reaction yield is further increased.

The invention claimed is:

1. A process for manufacturing 2-[(3,5-difluoro-3'-methoxy-1,1'-biphenyl-4-yl)amino]nicotinic acid, which comprises the steps of:
   a) providing 3,5-difluoro-3'-methoxybiphenyl-4-amine,
   b) preparing and isolating an aminium salt of the 3,5-difluoro-3'-methoxybiphenyl-4-amine, and
   c) further reacting the aminium salt of 3,5-difluoro-3'-methoxybiphenyl-4-amine obtained in b) to obtain 2-[(3,5-difluoro-3'-methoxy-1,1'-biphenyl-4-yl)amino] nicotinic acid.

2. The process according to claim 1, wherein in step a) 3,5-difluoro-3'-methoxybiphenyl-4-amine is obtained by reacting 4-bromo-2,6-difluoroaniline with 3-methoxyphenylboronic acid.

3. The process according to claim 1, wherein step c) comprises the step of
   c1) reacting the aminium salt of 3,5-difluoro-3'-methoxybiphenyl-4-amine obtained in step b) with 2-chloronicotinic acid, or
   c2) hydrolysing the aminium salt of 3,5-difluoro-3'-methoxybiphenyl-4-amine obtained in step b) to obtain 3,5-difluoro-3'-methoxybiphenyl-4-amine,
   and reacting the thus-obtained 3,5-difluoro-3'-methoxybiphenyl-4-amine with 2-chloronicotinic acid.

4. The process according to claim 1, wherein the aminium salt in step b) is formed by mixing a mineral acid or an organic acid with a solution or suspension of the 3,5-difluoro-3'-methoxybiphenyl-4-amine, in a solvent chosen from $C_5$-$C_8$ alkanes, $C_1$-$C_8$ haloalkanes, alcohols, esters, ethers, water, and mixtures thereof.

5. The process according to claim 4, wherein:
   the mineral acid is chosen from hydrobromic acid, hydrochloric acid, hydrofluoric acid, nitric acid, phosphoric acid, sulfuric acid and mixtures thereof; and/or
   the organic acid is chosen from cyclamic acid, ethane-1,2-disulfonic acid, methanesulfonic acid, naphthalene-1,5-disulfonic acid, naphthalene-2-sulfonic acid, thiocyanic acid, formic acid, acetic acid, p-toluenesulfonic acid, 4-chloro benzenesulfonic acid, 4-bromo benzenesulfonic acid and mixtures thereof; and/or
   the solvent is chosen from pentane, n-hexane, n-heptane, n-octane, chloromethane, dichloromethane, tetrachloromethane, ethanol, n-propanol, isopropanol, n-butanol, isobutanol, sec-butanol, t-butanol, n-pentanol, tert-pentyl alcohol (tert-amyl alcohol), ethylene glycol, propylene glycol, dipropylene glycol, glycerol, diethylene glycol monoethyl ether, n-propyl acetate, isopropyl acetate, butyl glycol acetate, water and mixtures thereof.

6. The process according to claim 4, wherein the ratio of the volume of the solvent in step b) to the mass of 4-bromo-2,6-difluoroaniline from step a) ranges from 2:1 to 50:1.

7. The process according to claim 3, wherein step c1) or c2) takes place in a solvent or mixture of solvents.

8. The process according to claim 7, wherein the solvent is chosen from ethanol, n-propanol, isopropanol, n-butanol, isobutanol, sec-butanol, t-butanol, n-pentanol, tert-pentyl alcohol (tert-amyl alcohol), ethylene glycol, propylene glycol, dipropylene glycol, glycerol, diethylene glycol monoethyl ether, tetrahydrofurane, 1,4-dioxane, 1,2-dioxane, 1,3-dioxane and mixtures thereof.

9. The process according to claim 3, wherein in step c1) or c2) a mineral acid chosen from hydrobromic acid, hydrochloric acid, hydrofluoric acid, nitric acid, phosphoric acid, sulfuric acid and mixtures thereof or an organic acid chosen from cyclamic acid, ethane-1,2-disulfonic acid, methanesulfonic acid, naphthalene-1,5-disulfonic acid, naphthalene-2-sulfonic acid, thiocyanic acid, formic acid, acetic acid, p-toluenesulfonic acid, 4-chloro benzenesulfonic acid, 4-bromo benzenesulfonic acid and mixtures thereof is added to the reaction mixture.

10. The process according to claim 9, wherein the acid is added in the form of an aqueous solution; and/or wherein the volume ratio of the solvent to the acid ranges from 1:5 to 1:15.

11. The process according to claim 1, which comprises the steps of:
   a) reacting 4-bromo-2,6-difluoroaniline with 3-methoxyphenylboronic acid to obtain 3,5-difluoro-3'-methoxybiphenyl-4-amine,
   b) forming and isolating an aminium salt of 3,5-difluoro-3'-methoxybiphenyl-4-amine obtained in step a) by mixing an acid chosen from hydrochloric acid, nitric acid, phosphoric acid, sulfuric acid, p-toluenesulfonic acid and mixtures thereof with a solution or suspension of 3,5-difluoro-3'-methoxybiphenyl-4-amine in a solvent chosen from n-hexane, dichloromethane, ethylene glycol, propylene glycol, n-propyl acetate, isopropyl acetate and mixtures thereof, and
   c1) reacting the aminium salt of 3,5-difluoro-3'-methoxybiphenyl-4-amine from step b) with 2-chloronicotinic acid.

12. The process according to claim 2, wherein step a) is catalyzed by a Pd/C catalyst.

13. A process for manufacturing 2-[(3,5-difluoro-3'-methoxy-1,1'-biphenyl-4-yl)amino]nicotinic acid, which comprises the steps of:
   i) reacting 4-bromo-2,6-difluoroaniline with 3-methoxyphenylboronic acid in the presence of a Pd/C catalyst to obtain 3,5-difluoro-3'-methoxybiphenyl-4-amine, and
   ii) further reacting the 3,5-difluoro-3'-methoxybiphenyl-4-amine obtained in step i) to obtain 2-[(3,5-difluoro-3'-methoxy-1,1'-biphenyl-4-yl)amino]nicotinic acid.

14. The process according to claim 13, wherein step ii) comprises
   b) preparing and isolating an aminium salt of the 3,5-difluoro-3'-methoxybiphenyl-4-amine, and
   c) further reacting the aminium salt of 3,5-difluoro-3'-methoxybiphenyl-4-amine obtained in b) to obtain 2-[(3,5-difluoro-3'-methoxy-1,1'-biphenyl-4-yl)amino] nicotinic acid.

15. The process according to claim 5, wherein the solvent is chosen from n-hexane, dichloromethane, ethylene glycol, propylene glycol, n-propyl acetate, isopropyl acetate, water, and mixtures thereof.

16. The process according to claim 6, wherein the ratio of the volume of the solvent in step b) to the mass of 4-bromo-2,6-difluoroaniline from step a) ranges from 5:1 to 25:1.

17. The process according to claim 10, wherein the acid is added in the form of an aqueous solution; and/or wherein the volume ratio of the solvent to the acid ranges from 1:2 to 1:10.

* * * * *